United States Patent [19]

Smith et al.

[11] Patent Number: 5,234,453
[45] Date of Patent: Aug. 10, 1993

[54] COBALT BASE ALLOY END EFFECTORS FOR LAPAROSCOPIC SURGICAL SCISSORS

[75] Inventors: Kevin W. Smith, Miami; Thomas O. Bales, Coral Gables, both of Fla.

[73] Assignee: Symbiosis Corporation, Miami, Fla.

[21] Appl. No.: 780,034

[22] Filed: Oct. 21, 1991

Related U.S. Application Data

[63] Continuation-in-part of Ser. No. 521,766, May 10, 1990, Pat. No. 5,133,727.

[51] Int. Cl.$^5$ ............................................. A61B 10/00
[52] U.S. Cl. ...................................... 606/170; 606/174
[58] Field of Search .................. 30/250, 251, 242, 155, 30/266, 335, 350; 128/749, 751; 606/205–208, 167, 170, 174; 403/279, 284, 282, 79

[56] References Cited

U.S. PATENT DOCUMENTS

| | | | |
|---|---|---|---|
| 3,816,920 | 6/1974 | Sastri | 30/350 |
| 3,895,636 | 7/1975 | Schmidt | 606/174 |
| 4,101,984 | 7/1978 | MacGregor | 606/72 |
| 4,760,848 | 8/1988 | Hasson | 606/174 |
| 4,950,273 | 8/1990 | Briggs | 606/205 |
| 5,069,872 | 12/1991 | Penoza | 30/350 |

Primary Examiner—Lee S. Cohen
Assistant Examiner—Samuel Gilbert
Attorney, Agent, or Firm—David P. Gordon

[57] ABSTRACT

End effector scissor elements for laparoscopic surgical instruments are provided in the form of investment case cobalt base alloy elements. The cobalt base alloy scissor elements are homogeneous in composition. Each element has in its as-cast form an elongate portion having an integral cutting edge. At least on of the scissor elements also has a through-hole transverse to the elongate portion. The scissor elements are arranged as scissor cutting instruments by opposing their cutting edges, and by engaging the through-hole of each pivoting element with apparatus coupled to an actuating push-rod of the laparoscopic surgical instrument. The preferred cobalt base alloy is a cobalt base superalloy with at least 38% cobalt, and preferably 50% or more cobalt. The cobalt base alloy should be sufficiently hard to scratch stainless steel.

29 Claims, 4 Drawing Sheets

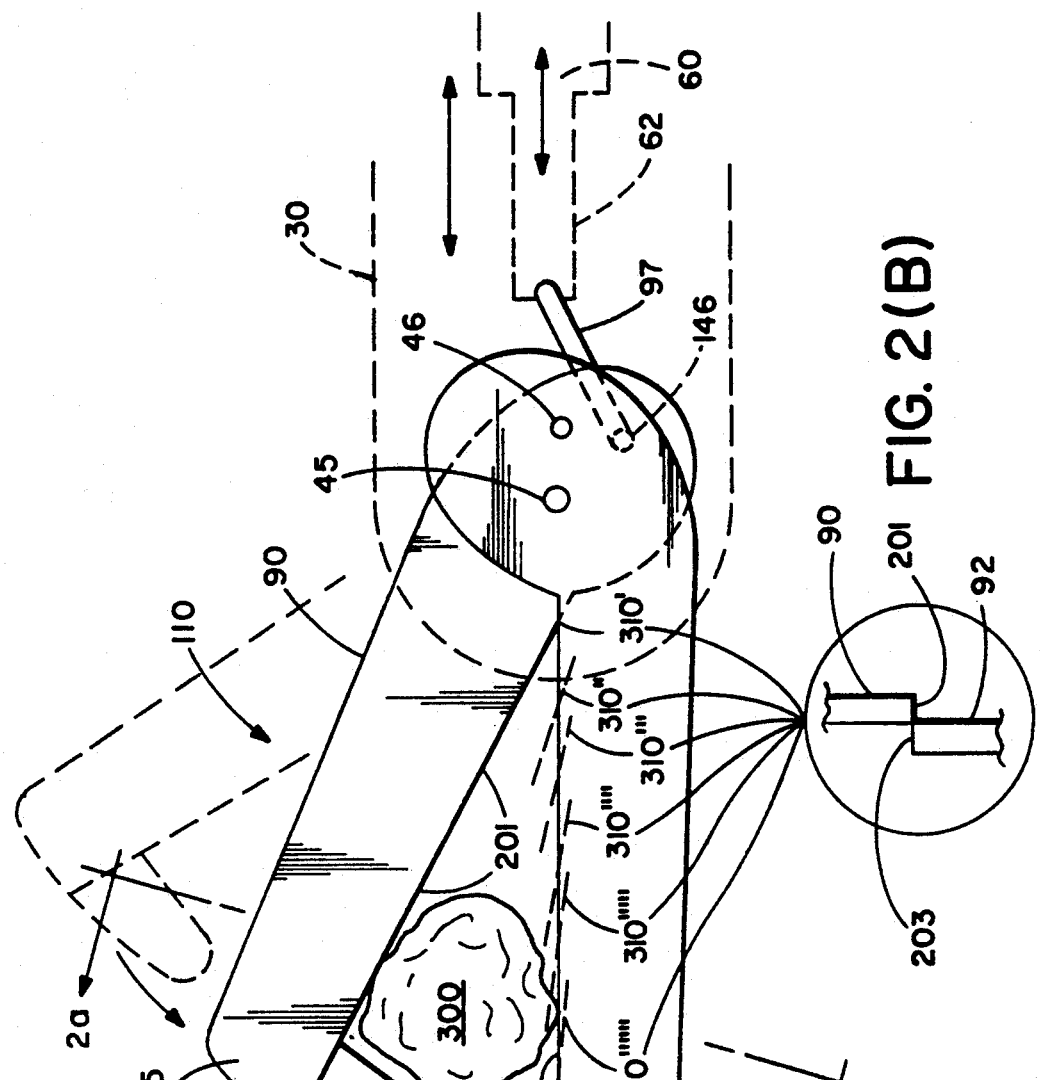
FIG. 2
FIG. 2(B)
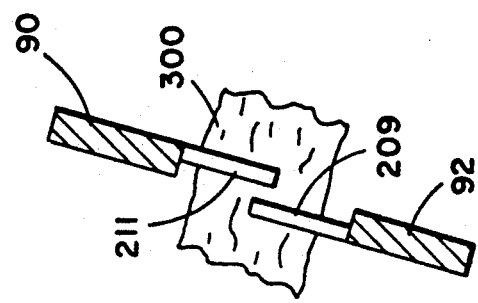
FIG. 2(A)

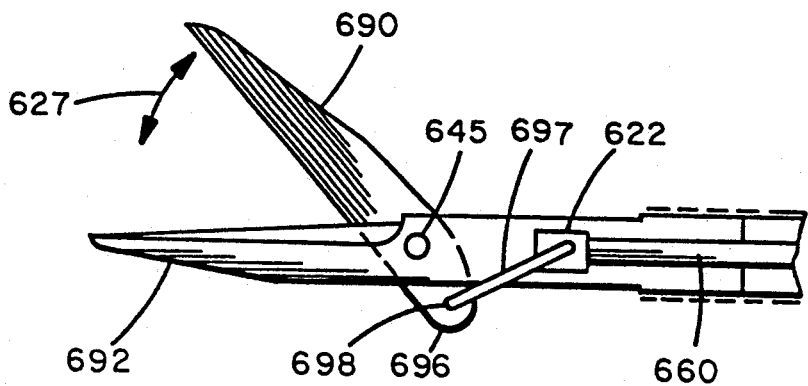
FIG. 4a
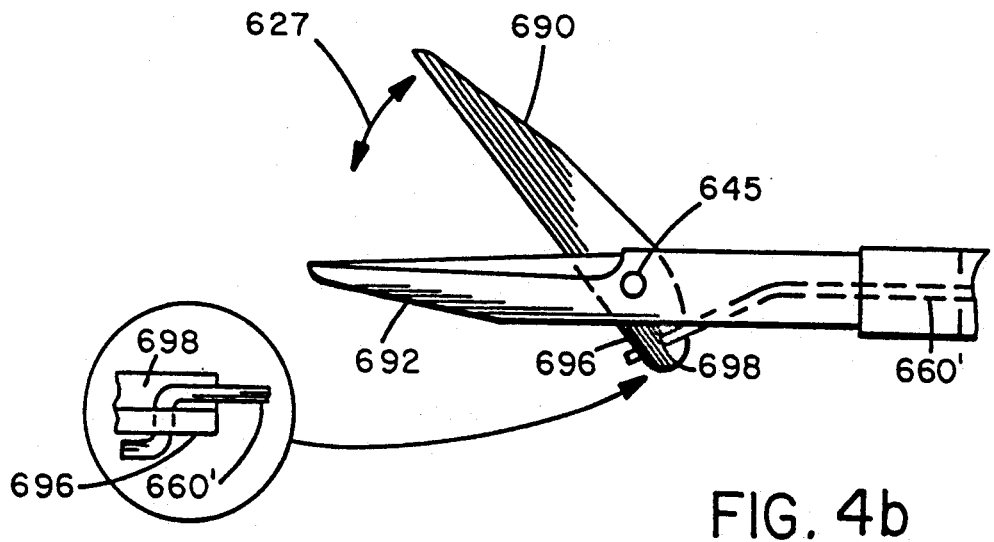
FIG. 4b
FIG. 4c

COBALT BASE ALLOY END EFFECTORS FOR LAPAROSCOPIC SURGICAL SCISSORS

This application is a continuation-in-part of Ser. No. 07/521,766, filed May 10, 1990 now issued as U.S. Pat. No. 5,133,727, and is related to Ser. Nos. 07/680,392, and U.S. Ser. No. 07/780,014, now issued as U.S. Pat. No. 5,171,258, and U.S. Ser. No. 07/780,013, all of which are incorporated by reference herein in their entireties.

BACKGROUND OF THE INVENTION

This invention broadly relates to laparoscopic surgical devices. More particularly, the invention relates to laparoscopic surgical scissor instruments where the scissor end effectors are uniformly comprised of a cobalt based alloy and are formed by casting.

The laparoscopy procedure has recently become a widely practiced surgical procedure. A laparoscopy procedure typically involves incising through the navel and through the abdominal wall for viewing and/or operating on the ovaries, uterus, gall bladder bowels, appendix, although more recently, incisions and insertion of trocar tubes have been made in different areas of the abdomen and even in the chest cavity. Typically, trocars are utilized for creating the incisions. Trocar tubes are left in place in the abdominal wall so that laparoscopic surgical tools may be inserted through the tube. A camera or magnifying lens is often inserted through the largest diameter trocar tube (e.g. 10 mm diameter) which is generally located at the navel incision, while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

The laparoscopic tools of the prior art are primarily reusable stainless steel tools. The use of stainless steel for surgical instruments started in the early 1900's. Recently, almost all surgical scissor type instruments, including laparoscopic scissors, use stainless steel exclusively. One reason for the broad usage of stainless steel which contains about 11–27% (and typically 12–18%) chromium, is that stainless steel is generally hard and highly resistant to corrosion. Stainless steel however, is not easily castable into small precision components. Thus, if an attempt is made to cast stainless steel parts such as precision end effectors for laparoscopic tools, invariably the stainless steel parts require finishing; i.e., buffing and polishing to remove imperfections. Also, while stainless steel is a hard material as represented by standard indentation tests, it is subject to scratching, and the narrow grooves resulting from scratching are disadvantageously the site of potential contamination. A further disadvantage of stainless steel end effectors is that they tend to break or nick upon the inadvertent cutting of surgical staples.

Recently, as disclosed in Ser. U.S. Pat. No. 5,133,727 and Ser. No. 07/680,392, investment cast bronze end effectors have been utilized to great advantage. However, because bronze is a relatively soft alloy, the use of investment cast bronze as end effector scissor elements is not advantageous.

SUMMARY OF THE INVENTION

It is therefore an object of the invention to provide cast end effector scissor elements which are harder than stainless steel.

It is another object of the invention to provide hard end effector scissor elements for a laparoscopic instrument which are readily castable and do not require additional machining.

It is a further object of the invention to provide investment cast end effector elements for a laparoscopic instrument which ar harder than stainless steel, corrosion resistant, and which do not require additional machining.

In accord with the objects of the invention, end effector scissor elements for laparoscopic surgical instruments are provided in the form of investment cast cobalt base alloy elements. The cobalt base alloy scissor elements, which are homogeneous in composition, each have in their as-cast form an elongate portion having an integral cutting edge. At least one of the scissor elements (and preferably both) also has a through-hole transverse to the elongate portion. The scissor elements are arranged as scissor cutting instruments by opposing their cutting edges, and by engaging the through-hole of each pivoting element with means coupled to an actuating push-rod of the laparoscopic surgical instrument.

While cobalt base alloys have been used in the past to make machining instruments, turbines, and the like, and have been cast formed as prosthetic devices, e.g., dental implants, and also used in wrought form as dental "picks" and the like, cobalt base alloy have not been cast for use as a homogeneous scissor elements, and most certainly have not been cast for use as homogeneous laparoscopic scissor elements.

While the preferred composition for a cobalt base alloy used as an end effector scissor element for a laparoscopic tool is 19–30% Cr, 0–35% Ni, 35–62% Co, 0–10% Mo, 0–15% W, 0–3% Ti, 0–0.6% Nb, 0–9% Fe, 0.4–0.6% C, 0–7.7% Ta, 0–4.5% Al, many commercially available cobalt base alloys are suitable. Preferably, the cobalt base alloy is a cobalt base superalloy; i.e., it contains chromium. Additional preferred elements include carbon, boron, and molybdenum. Other preferred aspects include the use of 38% or more cobalt in the alloy, and preferably 50% or more. Regardless of the exact composition, the cobalt base alloy is preferably sufficiently hard to scratch even the hardest stainless steel and to resist damage from titanium or stainless steel clips or staples.

Additional objects and advantages of the invention will become apparent to those skilled in the art upon reference to the detailed description taken in conjunction with the provided figures.

BRIEF DESCRIPTION OF THE DRAWINGS

FIG. 1a is a cross-section through the laparoscopic instrument of FIG. 1 at the indicated location;

FIG. 2 is an enlarged side elevation view, of illustrative laparoscopic hook scissors end effectors in an open position;

FIG. 2a is a front view of the end effectors of FIG. 2 along the arrows 2a—2a of FIG. 2;

FIG. 2b is a cross-sectional view of the blades of FIG. 2 at their point of closing as indicated in FIG. 2;

FIGS. 4a and 4b are side elevation views of first and second embodiments of illustrative single acting straight blade scissors in conjunction with clevis means, and the distal ends o rods and tubes of illustrative disposable laparascopic tools; and FIG. 4c is a partial bottom view of the connection of the push rod and end effector of FIG. 4b.

DETAILED DESCRIPTION OF INVENTION

Figure 1:
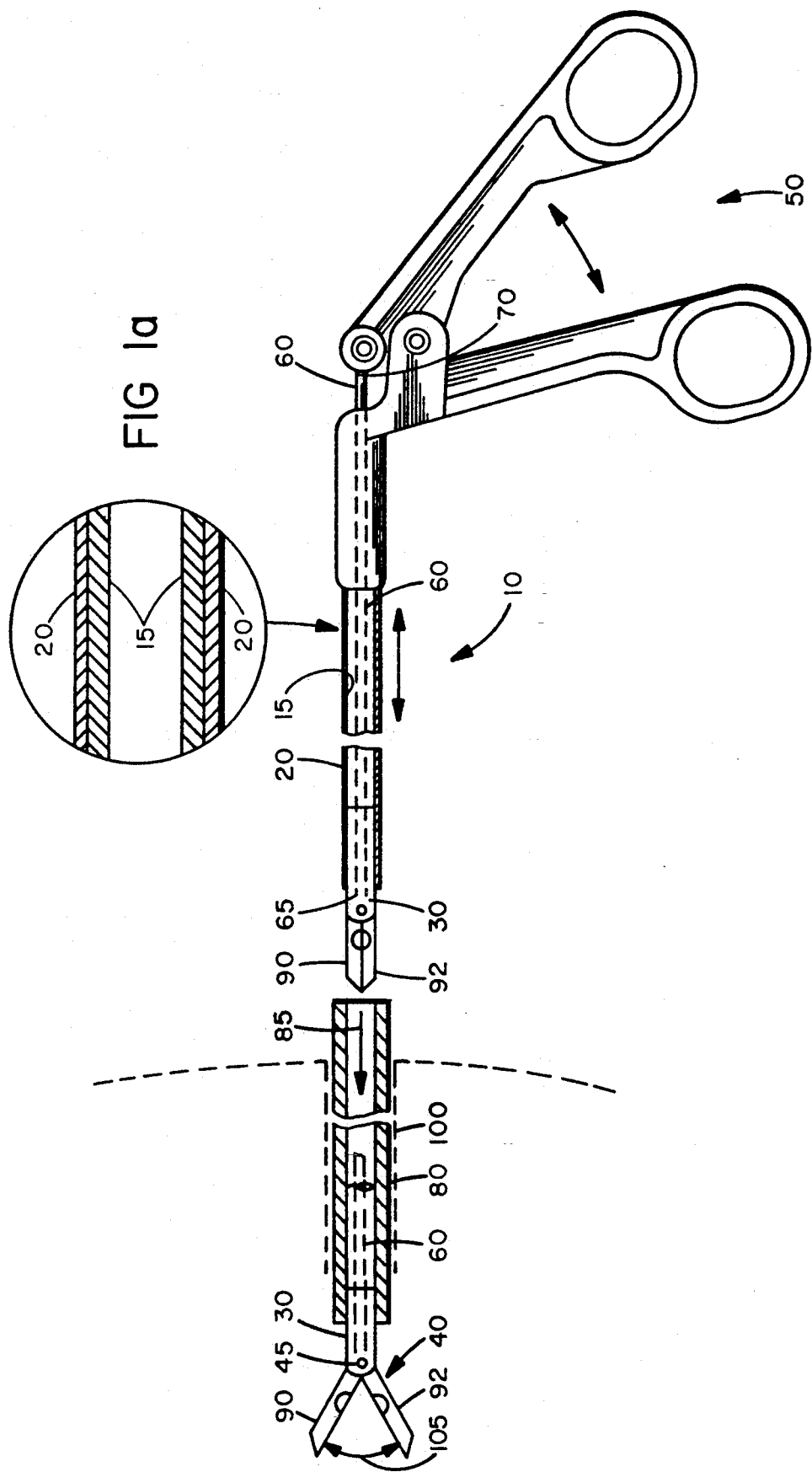
FIG. 1 is a side elevation view, partly in section, of a disposable laparoscopic instrument prior to insertion into a trocar tube, and, in partial phantom format, after insertion into a trocar tube.

With reference to FIGS. 1 and 1a, a disposable laparoscopic surgical instrument is indicated at 10. The disposable laparoscopic surgical instrument 10 broadly comprises an aluminum tube 15 surrounded by a peripheral insulating shrink wrap layer plastic 20, a clevis means 30, scissor element end effectors 40, actuating means 50, and a push rod 60. The clevis means 30 is preferably a separately formed aluminum piece which fixedly engages aluminum tube 15. The clevis 30 also engages the end effectors 40 which are pivotally engaged to clevis 30 at pivot pin 45. Rather than forming the end effectors 40 out of investment cast bronze as disclosed in previously incorporated Ser. No. 07/680,392, in accord with the present invention the end effectors 40 are formed out of investment cast cobalt base alloy as will be discussed in detail hereinafter. The push rod 60, which is preferably formed of stainless steel, is coupled at its distal end 65 to the end effectors 40, and is connected at 70, at its proximal end to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the scissor blades 90, 92 of the end effector 40 n the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, the blades 90, 92 can be opened and closed as indicated at 105 by reciprocal motion of push rod 60 which results from operation of the manual actuating means 50. As is discussed more fully in previously incorporated Ser. No. 07/680,392, the clevis helps translate the reciprocal motion of the push rod 60 into the end effector means action indicated at 105.

As previously mentioned, in accord with the present invention, the end effectors of the laparoscopic scissor devices of the invention are homogeneous cast devices which are comprised of a cobalt base alloy. The invention encompasses any and all different types of scissors. For example, as shown in FIGS. 2, 2a, 3, 3(A) and 3(B), and described more completely in previously incorporated Ser. No. 07/780,013, the scissors end effectors can be hook scissors having end effector elements (blades) 90, 92 with each end blade having respective cutting edges 201, 203 having terminal distal portions 205, 207. As the hook scissors shown in FIGS. 2, 2a, 3, 3(A), and 3(B) is a single acting scissors, only one of the blades absolutely requires a through-hole 145 (for pivot pin 45) transverse to the elongate blade element around which the blade can pivot, as the other blade can be integral with the clevis means if desired. Of course, with a double acting scissors (as indicated in FIG. 1), each blade would require such a transverse through-hole around which the blade could pivot. Also, each pivoting blade is preferably provided with a second through-hole 146 in which is engaged one end of a metal link member 97. The other end of the metal link member 97 is engaged to the flattened end 62 of push rod 60.

As shown in FIG. 2, and in the preferred embodiment of the laparoscopic scissors, the fixed blade member 92 of the hook scissors also engages pivot pin 45, as in the preferred embodiment both blade members are separately formed and neither is integral with the clevis means. By having both blade members have in-line through-holes 145 through which the pivot pin 45 extends, the blade members 90, 92 can be held in a tight bearing contact and can pivot. In order to prevent rotation or movement of a fixed blade such as blade 92 of FIG. 2, in the embodiment of the hook scissors of FIG. 2, blade member 92 is provided with a post 46 which engages a through-hole 146 in clevis 30. Thus, with blade member 92 fixed at two points (pin 45 and post 46) relative to clevis means 30, the blade member 92 is fixed in position with respect to clevis 30.

Figure 3B:
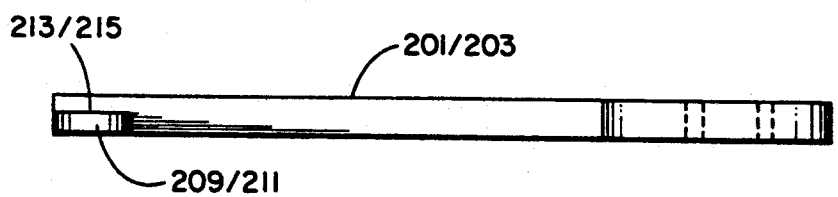
FIGS. 3, 3(A) and 3(B) are enlarged elevation, plan and side views of one of the blades of the device of FIG. 2.
Figure 3A:
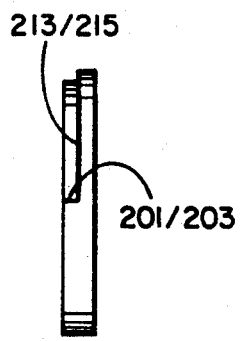
Figure 3:
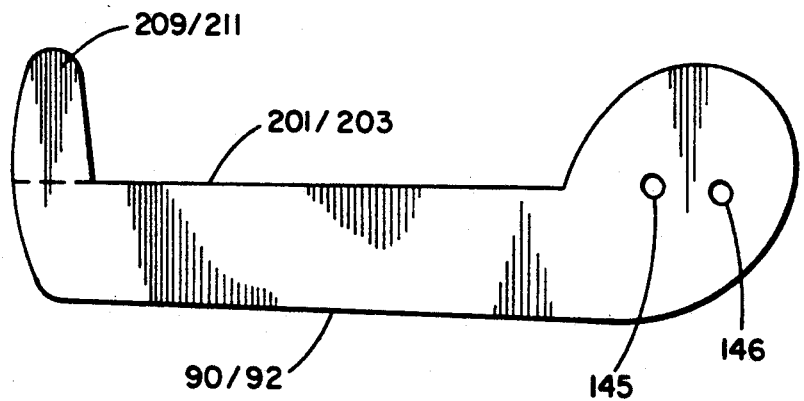

The blade members 90, 92 of the hook scissors end effectors of FIG. 2 are substantially identical. Minor differences include the provision of the projection or post 46 on fixed blade 92 for insertion into a hole in the clevis (not shown), and the elimination of hole 146 on blade 92 as no connection of blade 92 is required to push rod 60. As seen in FIG. 3, each elongate straight blade member 90, 92 has a transverse integral hook element 209, 211. The hook elements 209, 211 extend toward each other in the open position of FIG. 2 and are offset from their respective blade members as indicated at 213, 215 of FIG. 3 to provide a narrow recess 217 between the opposing hook elements when the blade members are closing or in the closed position.

Turning to FIGS. 4a and 4b, different laparoscopic scissor devices are shown. FIG. 4a shows a single acting straight scissors with blades 690 and 692, clevis 630″, post 645, and with a connecting means 697 extending through hole 698 in the proximal end 696 of blade 690. The connecting means 697 couples the pivoting blade 690 to the flattened end 622 of rod 660″. While blade 692 is stationary and can be integral with the clevis 630″, blade 690 pivots as indicated at 627 around pin 645. To ensure rotational movement of blade 690 upon axial movement of rod 660″, the end 622 of rod 660″ should be supported.

FIG. 4b shows a second embodiment of a single acting straight scissors having blades 690 and 692 and pivot post 645 which extends through holes in blades 690 and 692. In FIG. 4b, however, instead of utilizing a pull rod with a flattened end as shown in FIG. 4a with a connecting means, instead, a pull rod 660′ is provided which has a very thin wire of staple thickness (e.g. 25 mils) and has a rigid dog's-leg or zigzagged end which extends through hole 698 of the proximal end 696 of scissor blade 690 (as seen best in FIG. 4c). In both embodiments of FIGS. 4a and 4b, transverse through-holes are provided in both blades 690 and 692. The through-holes are preferably in register and scissor action is provided by reciprocal movement of the push-rod of the laparoscopic instrument as described in the above noted co-pending applications.

Other single acting laparoscopic scissors, including, but not limited to straight scissors and hook scissors are intended to be encompassed by the invention. The invention is also intended to encompass scissors using different mechanisms for causing rotation of the blade(s) to effect a cutting action. For example, the scissors can be arranged to be a double acting dual pivot scissors with arrangements more particularly described in Ser. No. 07/780,014.

In making end effectors for a laparoscopic scissors tool according to the invention, a precise pattern of the end effector element (including an elongate cutting edge and at least one through-hole in the base portion) s made from wax or suitable decomposable plastic known to the "lost wax" casting art. The pattern is dipped into or covered with slurried refractory material and dried to form the investment mold using well known techniques such as those used for casting jewelry and small sized machinery components. The pattern is melted or burned out of the investment mold, and molten cobalt base alloy is then poured into the mold and solidified therein. After solidification the investment mold is broken away from the cobalt base alloy casting and the as-cast element is ready for use as an end effector without requiring post-casting mechanical finishing operations on the elongated portion and its cutting edge other than to hone or fine grind the cutting edge. It should be noted that to avoid defects which might clog the through-holes in the end effectors, vacuum investment techniques known in the casting arts are preferably utilized.

The material of the investment cast end effector elements of the present invention is a cobalt base alloy in which cobalt is the predominate element; i.e., there is more cobalt by weight in the alloy than any other element. Particularly suitable cobalt base alloys are those in the category of superalloys which contain in addition to cobalt a significant amount of chromium and are characterized by resistance to oxidation and hot corrosion. Preferred alloy compositions for the end effectors of the present invention are cobalt base alloys containing at least about 38% by weight cobalt and more preferably at least about 50% by weight cobalt. A carbon content of between about 0.45-0.55% by weight carbon is preferred for increased hardness. The inclusion of small amounts of boron up to about 0.007% by weight also increases hardness. A chromium content of about 20-30% by weight is preferred to ensure high long term corrosion resistance. The cobalt base alloy investment cast end effectors of the present invention have a hardness such that the cutting edge of the end effector will scratch stainless steel leaving a minute groove but will not themselves be scratched by stainless steel or titanium. This is an important feature of the present invention since in the course of a laparoscopic procedure the scissors may close on or contact a stainless steel or titanium staple. In such case the scissor end effector elements are not marred and there is no damage to the cutting edges.

The preferred cobalt base superalloy for practicing the invention is alloy 5385 of Cannon Muskegon which is modified to contain between 0.46 and 0.55% Carbon. In particular, an alloy having the following elements is preferred:

61.24% Co 28.6% Cr 5.28% Mo 2.66% Fe .91% Si .54% C .50% Mn .25% Ni <.01% P <.005% S <.005 B

Other alloys believed to be suitable for practicing the present invention are:

58% Co 21% Cr 11% W 3.5% Al 2.5% Fe 2% Ta 1% Ni .5% Mn .45% C .1% Y (sold as AR-13)
66% Co 19% Cr 6.5% Ta 4.7% W 3.5% Al .18% C .01% Zr .1% Y (sold as AR-213)
64% Co 19% Cr 7.5% Ta 4.5% W 4.3% Al .35% C .13% Zr .17% Y (sold as AR-215)
52% Co 29% Cr 10% Ni 7.5% W 1% Fe .25% C .01% B (sold as FSX-414)
19-21% Cr 14-16% W 9-11% Ni 3% max Fe 1-2% Mn 1% max Si .05-.15% C .03% P .03% max S rem Co (sold as Haynes 25)
20-24% Cr 20-24% Ni 13-16% W 3% max Fe 1.25 max Mn .2-.5% C .03-.15% La rem Co (sold as Haynes 188)
Typical
58% Co 21.5% Cr 10% W 9% Ta .85% C .005% B .2% Zr
Range
20-23% Cr 9-11% W 8-10% Ta .78-.93% C .75-1.5% Fe .1-.4% Si .1-.3% Zr .1% max Mn .01 max B rem Co (sold as MAR-M 302)
Typical
61% Co 21.5% Cr 9% W 4.5% Ta .75% Ti 1% C 2.25% Zr
Range
20-23% Cr 8-10% W 4-5% Ta 2-2.5% Zr .9-1.1% C .65-.85% Ti 1.5% max Fe .2% max Mn .2% max Si rem Co (sold as MAR-M 322)
Typical
55% Co 23.5% Cr 10% Ni 7% W 3.5% Ta .2% Ti .6% C .5% Zr
Range
21-24% Cr 9-11% Ni 6.5-7.5% W 3-4% Ta .55-.65% C .4-.6% Zr .25-.25% Ti 1.5% max Fe .4% max Si .1 max Mn .01 max B .015 max S rem Co (sold as MAR-M 509)
28-32% Cr 3.5-5.5% W 3% max Fe 3% max Fe 3% max Ni 2% max Mn 2% max Si 1.5% max Mo .9-1.4% C rem Co (sold as Haynes Stellite 6B)
28-32% Cr 3.5-5.5% W 3% max Fe 3% max Ni 2% max Si 2% max Mn 1.4-1.9% C 1.5% max Mo rem Co (sold as Haynes Stellite 6K)
48-52% Co 27-29% Cr .5-1% Mn .5-1% Si .5-.12% C .02 max P .02% max S rem Fe (sold as Haynes Alloy #150)
54% Co 25.5% Cr 10.5% Ni 7.5% W .75% Mn .75% Si .5% C (sold as X-40/X-45).

Of course, cobalt base alloys other than those provided above can be utilized. The primary requirement for the cobalt base alloy is that, regardless of composition, it should be sufficiently hard to scratch stainless steel. Typically, such a cobalt base alloy will comprise a cobalt base superalloy; i.e., it contains chromium. As may be seen from the provided examples, additional preferred elements include carbon, boron, and molybdenum. Also, as may be seen from the provided examples, the cobalt base alloy will typically include the use of 38% or more cobalt in the alloy. Preferably, the chosen alloy will contain 50% or more cobalt. Other considerations in choosing a cobalt base alloy are that the alloy should be readily castable, hard but not too brittle, and corrosion resistant. Of additional benefit is an alloy which when cast will not require additional machining.

Preferably, the cobalt base alloys are used for laparoscopic scissor blades having a length of less than 0.75 inches from the transverse through-hole to the end of the blade, a height less than 0.40 inches, and a thickness less than 0.20 inches, although they the cobalt base alloy is suitable for other size blades.

There have been described herein laparoscopic scissor instruments utilizing end effectors comprised of cobalt base alloys. While particular embodiments of the invention have been described, it is not intended that the invention be limited thereto, as it is intended that the invention be as broad in scope as the art will allow and that the specification be read likewise. Thus, while particular cobalt base alloys were described, it will be appreciated that other cobalt base alloys can be utilized. Also, while particular laparoscopic tools were described which utilize particular mechanisms, it will be appreciated that the invention applies to all laparoscopic scissors regardless of the mechanisms utilized, provided that the cutting blades are uniformly made of a cobalt base alloy. In particular, the scissor end effectors can include a blade which is integral with the clevis, or two separate blades, blades which pivot based on a dual pivot point design, blades which pivot based on a single pivot point design, blades which are connected to the push rod by connecting means, and blades which are directly connected to the push rod means. Therefore, it will be appreciated by those skilled in the art that yet other modifications could be made to the provided invention without deviating from its spirit and scope as so claimed.

We claim:

1. A scissors device comprising:
   a) a pair of investment cast homogeneous scissor elements each comprised of a cobalt based alloy, each said investment cast homogeneous scissor element having in its as-cast form an elongate portion having an integral cutting edge and an adjacent base portion, and at least one of said investment cast homogeneous scissor elements having a through-hole in said base portion transverse to said elongate portion, wherein said pair of investment cast homogeneous scissor elements are laterally offset one to the other with respective said integral cutting edges oppositely adjacent each other, and each said scissor element has a length, a height, and a thickness, said height being less than about 0.4 inches, and said thickness being less than about 0.2 inches; and
   b) a pivot means extending transverse said pair of investment cast homogeneous scissor elements and extending through said through-hole of said at least one of said scissor elements, said pivot means for permitting pivoting of at least one of said pair of investment cast homogeneous scissor elements relative to the other or said pair of scissor elements.

2. A scissors device according to claim 1, wherein: said cobalt base alloy is a cobalt base super alloy.

3. A scissors device according to claim 2, wherein: said cobalt base alloy contains about 20 to 30% by weight chromium, and said cobalt base alloy contains at least about 38% by weight cobalt.

4. A scissors device according to claim 3, wherein: said cobalt base alloy contains about 0.45 to 0.55% by weight carbon.

5. A scissors device according to claim 4, wherein: said cobalt base alloy consists essentially of, in weight percent, about 25–29% Cr, 2–3% Fe, 5–6% Mo, up to 0.04% P,, up to 0.007% B, up to 1% Ni, up to 1% Mn, up to 1% Bi, balance Co and trace amounts of incidental impurities.

6. A scissors device according to claim 5, wherein: said cobalt base alloy consists essentially of 28.6% Cr, 2.7% Fe, 5.3% Mo, 0.54% C, 0.25% Ni, 0.91% Bi, 0.5% Mn, less than 0.01% P, 0.005% S, 0.005% B, balance Co in an amount of at least 61.2%.

7. A scissors device according to claim 1, wherein: said cobalt base alloy contains at least about 38% by weight cobalt.

8. A scissors device according to claim 1, wherein: said cobalt base alloy contains at least about 50% by weight cobalt.

9. A scissors device according to claim 1, wherein: each said investment cast homogeneous end effector has a said transverse through-hole, and each said investment cast homogeneous end effector has a length less than about 0.75 inches from said transverse through-hole to the end of said end effector.

10. A scissors device according to claim 1, wherein: said cutting edge of said element is hard enough to scratch stainless steel.

11. In a surgical instrument for insertion through a trocar, tube, and having an outer tube having a longitudinal axis, first and second scissor end effector elements coupled to said outer tube, with at least one of said first and second scissor elements rotating around an axis perpendicular to said longitudinal axis, and an actuating means extending through said outer tube and coupled to at least said rotating scissor element for effecting rotation thereof by movement of said actuating means, an improvement comprising:
   said first and second end effector elements are each comprised of a cobalt base alloy, each end effector in the form of a homogeneous cast blade having in its as-cast form an elongate portion, and at least one of said end effector elements having a through-hole transverse to said elongate portion, said first and second end effector elements being laterally offset relative to each other and having their respective cutting edges opposite each other wherein said rotation of at least one of said first and second end effector elements effects a scissoring action.

12. In a surgical instrument according to claim 11, wherein:
   said surgical instrument further comprises a clevis coupled to said outer tube and having a pivot perpendicular to said longitudinal axis and,
   said surgical instrument is a double acting instrument, and both said first and second end effector elements have through-holes and are pivotally engaged at their respective through-holes to said pivot, and both said first and second end effector elements are coupled to said actuation means.

13. In a surgical instrument according to claim 11, wherein:
   said cobalt base alloy is a cobalt base superalloy containing at least about 38% by weight cobalt.

14. In a surgical instrument according to claim 13, wherein:
   said cobalt base alloy consists essentially of by weight, 25–29% Cr, 2–3% Fe, 5–6% Mo, up to 0.04% P,, up to 0.007% B, up to 1% Ni, up to 1% Mn, up to 1% Bi, balance Co and trace amounts of incidental impurities.

15. In a surgical instrument according to claim 14, wherein:
   said cobalt base alloy consists essentially of 28.6% Cr, 2.7% Fe, 5.3% Mo, 0.54% C, 0.25% Ni, 0.91% Bi, 0.5% Mn, less than 0.01% P, 0.005% S, 0.005% B., balance Co in an amount of at least 61.2%.

16. In a surgical instrument according to claim 11, wherein:

said cutting edge of said first and second end effector is hard enough to scratch stainless steel.

17. In a surgical instrument according to claim 11, wherein:
said first and second end effector elements each have a length, a height, and a thickness, said length being less than 0.75 inches from said transverse through-hole to the end of said end effector element, said height being less than 0.40 inches, and said thickness being less than 0.20 inches.

18. In a surgical instrument according to claim 11, wherein:
said cobalt base alloy is a cobalt base super alloy.

19. In a surgical instrument according to claim 11, wherein:
said cobalt base alloy contains about 0.45 to 0.55% by weight carbon.

20. A surgical scissors, comprising:
a) a hollow tube having a first end and a second end;
b) a clevis coupled to said first end of said hollow tube;
c) two homogeneous cast end effector scissor elements, at least one of said scissor elements pivotally engaging said clevis, said scissor elements being laterally offset relative to each other and having respective cutting edges arranged opposite each other;
d) a rod extending at least partially through said hollow tube and having a first end and a second end, said first end of said rod being coupled to at least said scissor element which pivotally engages said clevis; and
e) actuating means engaged to said second end of said rod for imparting reciprocal motion to said rod relative to said tube which is translated at said clevis to pivotal motion of said pivotally engaged scissor element, wherein
said at least one scissor element which pivotally engages said clevis has a base portion having a through-hole therethrough which is used to couple said rod to said at least one scissor element, and said at least one scissor element which pivotally engages said clevis has a length, a height, and a thickness, said height being less than about 0.4 inches, and said thickness being less than about 0.2 inches, and
said two cast end effector scissor elements are comprised of a cobalt base alloy.

21. A surgical scissors according to claim 20, wherein:
said through-holes in said base portion of said scissor elements are coaxial with each other.

22. A surgical scissors according to claim 21, wherein:
said homogeneous cast end effector scissor elements are investment cast homogeneous elements,
said cobalt base alloy is a cobalt base superalloy containing at least about 38% by weight cobalt, and
said cutting edges of said end effector scissor elements are hard enough to scratch stainless steel.

23. A surgical scissors according to claim 20, wherein:
said cobalt base alloy is a cobalt base super alloy.

24. A surgical scissors according to claim 23, wherein:
said cobalt base alloy contains at least about 38% by weight cobalt.

25. A surgical scissors according to claim 23, wherein:
said cobalt base alloy contains at least about 50% by weight cobalt.

26. A surgical scissors according to claim 23, wherein:
said cobalt base alloy contains about 20 to 30% by weight chromium, and said cobalt base alloy contains at least about 38% by weight cobalt.

27. A surgical scissors according to claim 26, wherein:
said cobalt base alloy contains about 0.45 to 0.55% by weight carbon.

28. A surgical scissors according to claim 27, wherein:
said cobalt base alloy consists essentially of, in weight percent, about 25-29% Cr, 2-3% Fe, 5-6% Mo, up to 0.04P,, up to 0.007% B, up to 1% Ni, up to 1% Mn, up to 1% Bi, balance Co and trace amounts of incidental impurities.

29. A surgical scissors according to claim 28, wherein:
said cobalt base alloy consists essentially of 28.6% Cr, 2.7% Fe, 5.3% Mo, 0.54% C, 0.25% Ni, 0.91% Bi, 0.5% Mn, less than 0.01% P, 0.005% S, 0.005% B, balance Co in an amount of at least 61.2%.

* * * * *

UNITED STATES PATENT AND TRADEMARK OFFICE
CERTIFICATE OF CORRECTION

PATENT NO. : 5,234,453
DATED : August 10, 1993
INVENTOR(S) : Kevin J. Smith and Thomas O. Bales It is certified that error appears in the above-identified patent and that said Letters Patent is hereby corrected as shown below:

On title page, item [73]

The Assignee "Symblosis" should read --Symbiosis--.

Signed and Sealed this

Twelfth Day of April, 1994

Attest:

BRUCE LEHMAN

*Attesting Officer*     *Commissioner of Patents and Trademarks*